(12) United States Patent
Thomas et al.

(10) Patent No.: US 8,721,561 B2
(45) Date of Patent: May 13, 2014

(54) METHOD AND APPARATUS FOR ANALYZING PULMONARY PERFORMANCE

(75) Inventors: Norman Thomas, Golden, CO (US);
Edmond Chu, Erie, CO (US)

(73) Assignee: nSpire Health, Inc., Longmont, CO (US)

( * ) Notice: Subject to any disclaimer, the term of this patent is extended or adjusted under 35 U.S.C. 154(b) by 1348 days.

(21) Appl. No.: 11/431,905

(22) Filed: May 10, 2006

(65) Prior Publication Data
US 2006/0258949 A1 Nov. 16, 2006

Related U.S. Application Data

(60) Provisional application No. 60/679,782, filed on May 10, 2005.

(51) Int. Cl.
*A61B 5/08* (2006.01)
*A61B 7/00* (2006.01)
*A61M 16/00* (2006.01)

(52) U.S. Cl.
USPC ............... 600/538; 600/532; 128/204.18

(58) Field of Classification Search
USPC ................................... 600/532, 538
See application file for complete search history.

(56) References Cited

U.S. PATENT DOCUMENTS

| 4,256,100 A * | 3/1981 | Levy et al. | 128/204.21 |
| 4,520,812 A * | 6/1985 | Freitag et al. | 128/204.25 |
| 4,573,462 A * | 3/1986 | Baum | 128/204.25 |
| 5,752,506 A | 5/1998 | Richardson | |
| 6,139,506 A * | 10/2000 | Heinonen | 600/532 |
| 7,201,166 B2 * | 4/2007 | Blaise et al. | 128/203.12 |
| 7,431,031 B2 | 10/2008 | Hete | |

FOREIGN PATENT DOCUMENTS

WO PCT/US06/18206 5/2008

OTHER PUBLICATIONS

Ferraris Respiratory, Eagle Comprehensive Pulmonary Laboratory, downloaded from http://www.groupferraris.com/ferrarisrespiratory/usa/products/pdfs/Eagle.pdf, 2 pages, 2005.

* cited by examiner

*Primary Examiner* — Patricia Mallari
*Assistant Examiner* — Michael R Bloch
(74) *Attorney, Agent, or Firm* — Cooley LLP

(57) ABSTRACT

A pulmonary testing device and method are provided that measure an inspired volume of a selected gas component. In one configuration, the selected gas component is injected into the device in an airway of the device upstream of a gas analyzer. The device has opposing open ends, one for the patient's mouth and the other for inspiration of air.

10 Claims, 4 Drawing Sheets

METHOD AND APPARATUS FOR ANALYZING PULMONARY PERFORMANCE

This application claims the benefit of U.S. Provisional Application No. 60/679,782, filed May 10, 2005, the entire disclosure of which is hereby incorporated herein by reference.

FIELD OF THE INVENTION

The invention relates generally to pulmonary function testing and particularly to a device and method for measuring pulmonary functions in real-time or near real-time using controlled sample gas injection into the gas delivery system.

BACKGROUND

It is becoming increasingly important for healthcare providers to determine accurately pulmonary functions and mechanics in patients due to the prevalence of pulmonary diseases such as chronic bronchitis and emphysema. Many of the tests for pulmonary functions and mechanics use the techniques of gas dilution. In these tests, the patient inspires a gas mixture of known composition, typically stored in pressurized gas tanks or cylinders supplied by gas manufacturers. Inside the patient's lungs, some of these gas components become diluted by the gas within the lungs prior to the inhalation and/or by diffusion of the gas components through the alveoli. Pulmonary function and lung mechanics information can be derived by measuring and analyzing the composition and volume of the gas the patient exhales. Trace gases in the inspired gas mixtures include carbon monoxide and acetylene (each of which is used to measure gas diffusion across the alveoli) and helium and methane (each of which is used to measure the dead space in the lung cavity and/or pulmonary testing device). As will be appreciated, carbon monoxide and acetylene absorb readily and rapidly into the bloodstream while helium and methane do not. In this case, the volumes of the carbon monoxide or acetylene component and the helium or methane in the inspired and/or expired gas are determined and used along with the known composition of the sample gas, to calculate the volume of carbon monoxide or acetylene absorbed by the lungs. Carbon dioxide concentration in the expired gas can also be measured to ascertain lung diffusion because the concentration of carbon dioxide is directly related to the amount of oxygen absorbed into the bloodstream.

A typical pulmonary testing device (e.g. Eagle™ from Ferraris Respiratory, Inc.) is shown in FIG. 1. The device 100 includes a breathing conduit 104 that includes a patient mouthpiece 108, first and second outlets 112 and 116 for the discharge of exhaled air and intake of ambient inhaled air, respectively, and a test gas intake assembly 120. Balloon valves 124 and 128 open and close respectively the outlets 112 and 116. The test gas intake assembly 120 comprises a diaphragm 132 biased by a spring 136 and connected to a closure arm 140 that opens and closes the test gas introduction port 144 of conduit 148 upon demand (referred to as a demand valve). When the patient closes the balloons 124 and 128 and inhales, the diaphragm 132 is drawn downwards and the closure arm 140 repositioned as shown by the dotted lines. In this position, the port 144 is opened, thereby introducing pressurized test gas of known composition into the device 100 via conduit 148. The test gas is subsequently inhaled by the patient via the patient mouthpiece 108.

The patient can exhale immediately or after a determined time, depending on the type of test being conducted. A series of gas component sensors denoted by block 152 measure the concentrations of various selected gas components in the inspired and/or expired gas stream(s). Additionally, a gas flow measuring device 156 measures the flow rate of the inspired and/or expired gas stream, as desired.

The volume of a gas component actually inspired by the patient is given by the following equation:

$$V_X = (V_F \times F_X) - [(F_X - F_A) \times V_{DS}]$$

where $V_F$ is the total gas volume actually inspired by the patient, $F_X$ is the fraction of the selected gas component in the tank volume, $F_A$ is the concentration of the selected gas component in the ambient atmosphere (or in the device 100 before the test), and $V_{DS}$ is the interior volume of device 100 (dead space volume).

If the gas component has negligible diffusion rate through the alveoli into the blood stream, exhaled gas concentration measurements will allow estimations of the lung volume at the start of inhalation. Using gas such as carbon monoxide that has a high diffusivity through the alveoli, exhaled gas concentration measurements will provide an estimate of the lung diffusion properties.

This device 100 can have disadvantages. For example, it can be complex, expensive, physically large and unwieldy, and difficult to use. It typically may not be used for a number of pulmonary tests, such as pulmonary tests conducted while the patient is exercising.

The pre-mixed gases used in pulmonary function and lung mechanics testing can also be costly. The logistics associated with the ordering, storing, and disposal of the specialized gas cylinders also add to the complexity of the operation of a pulmonary function laboratory.

SUMMARY

These and other needs are addressed by the various embodiments and configurations of the present invention. The present invention can measure a variety of lung functions and mechanics using a breathing device in which the test gas is introduced without the use of demand valves.

In one embodiment, the device uses open, opposing ends and is free of valves, such as demand valves, positioned in the breathing. Inhalation of test gas is effected by the use of gas injectors. The gas delivery system can be digitally controlled to provide a test gas at varying flow rates and compositions.

Due to the use of rapid gas analyzers, the accuracy of the measurements does not depend on the assumption that the inspired gas composition is consistent.

In accordance with one embodiment, the test gas is stored in small single or multi-use cartridges and is provided to the patient during inhalation. The cartridges are substantially smaller than specialized gas cylinders of the prior art and thus may be easily stored and used in virtually any medical setting.

The device of the present invention can have a number of advantages. For example, it can be simple, lightweight, inexpensive, physically small, and easy to use. It can be digitally controlled and provide variable gas compositions at variable flow rates. The device can be readily adapted to a variety of pulmonary and cardiac tests, including stress testing. It can provide an extremely low resistance to patient inspiration, which can be important not only for test accuracy but also for patients with chronic lung conditions.

In accordance with one embodiment of the present invention, a pulmonary testing device is provided, comprising:

(a) first and second ends, the first end comprising a mouthpiece for a patient and the second end being open to the ambient atmosphere;

(b) at least one test gas injector positioned proximate the second end, the injector being angled away from the first end, whereby test gas is introduced in a direction away from the first end;

(c) a flow rate measuring device operable to determine a flow rate of gas being at least one of inspired and expired by the patient; and (d) a gas analyzer operable to measure an amount of a selected gas component.

The at least one test gas injector may be positioned in and/or near the second end such that the gas injector can provide test gas to the second end.

These and other advantages will be apparent from the disclosure of the invention(s) contained herein.

The above-described embodiments and configurations are neither complete nor exhaustive. As will be appreciated, other embodiments of the invention are possible utilizing, alone or in combination, one or more of the features set forth above or described in detail below.

DETAILED DESCRIPTION

Figure 1:
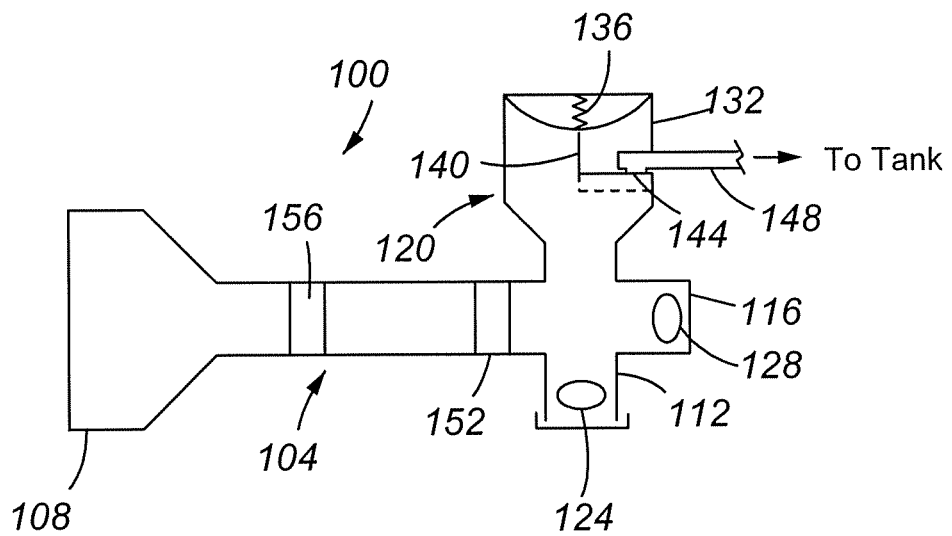
FIG. 1 is a cross-sectional view of a pulmonary testing device according to the prior art.
Figure 2B:
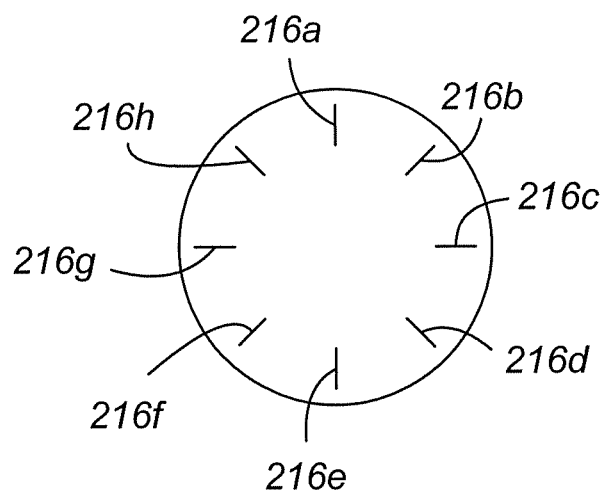
FIG. 2B is a cross-sectional view taken along line 2B-2B of FIG. 2A.
Figure 2A:
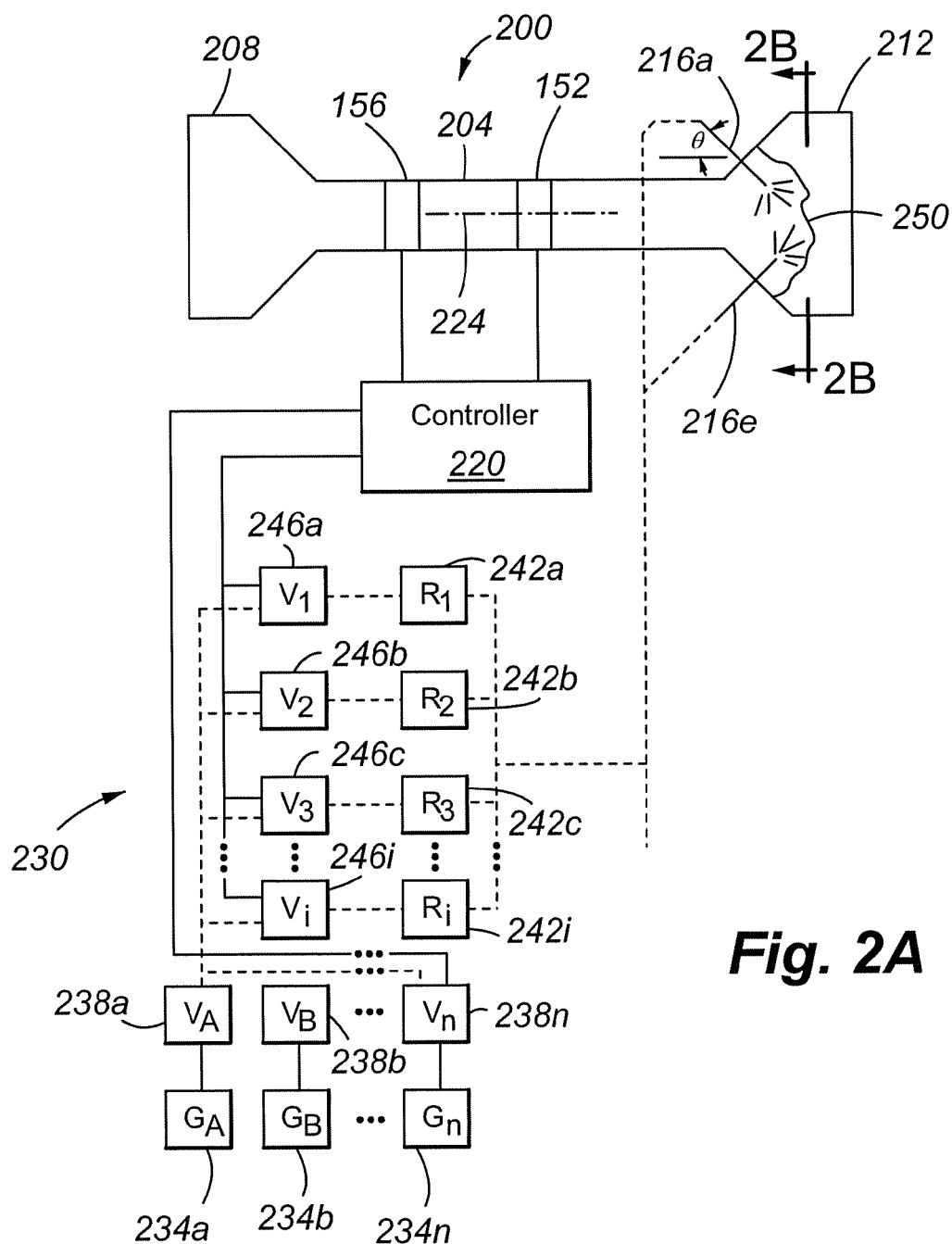
FIG. 2A is a cross-sectional view of a pulmonary testing device according to an embodiment of the present invention.

Referring to FIGS. 2A and 2B, a first embodiment of the pulmonary testing device 200 of the present invention will be discussed. The device includes a breathing conduit 204 having a patient mouthpiece 208 on one end and a test gas introduction inlet 212 on the other end. A plurality of injectors 216a-h are positioned in the test gas introduction inlet 212 to provide desired test gases into the inlet 212 from a pressurized gas source. Positioned between the two ends of the conduit 204 are gas flow measuring device 156 and a set of gas component sensors or gas analyzers denoted by block 152. A controller 220 receives measurement signals from the device 156 and sensors, uses the measurements to determine pulmonary (lung) parameters, such as diffusion, and lung capacity, and, based thereon, control test gas introduction or flow rates through the injectors 216a-h and controls the test gas composition provided to the injectors 216a-h, the injection of the test gas during inspiration, and the termination of test gas injection during expiration.

The breathing conduit 204 is open at either end and preferably provides little, if any, resistance to patient inhalation (which can be important for patients with chronic lung conditions). In other words when test gas is not being introduced through the injectors, the patient can breathe ambient air by placing his mouth over the mouthpiece 208 and inhaling, which will draw ambient air through the open inlet 212. It is also desirable for breathing conduit 204 to have a small volume (dead space) to minimize the amount of re-breathed gas. The conduit 204 can be of any composition but preferably is plastic.

The injectors 216a-h preferably have an outlet orifice that is smaller than the diameter of the body of the injectors 216a-h to introduce the test gas into the inlet 212 at a higher velocity than the flow velocity through the injector body. The injectors are preferably angled away from the patient to introduce gas in a direction of flow that is away from the patient. This injector orientation avoids forcing test gas into the patient's lungs, which would otherwise decrease the accuracy of the test. Preferably, the angle θ measured relative to the horizontal center line 224 of the conduit 204 is less than 90 degrees and more preferably ranges from about 10 to about 75 degrees. Although eight injectors 216a-h are depicted in FIG. 2B, it will be appreciated that any number or configuration of injectors may be used so long as the test gas wall 250 is maintained. Moreover though variable flow rate injectors are discussed herein, it is to be understood that fixed flow rate injectors may be used with the fixed flow rate being sufficient to maintain the test gas wall 250.

The gas flow measuring device 200 can be device capable of measuring gas flow, including without limitation a pneumatach, an ultrasonic emitter and receiver, a variable orifice, a transducer, and combinations thereof.

The gas sensors or analyzers 152 typically include a plurality of gas sensors for measuring each selected gas component. The sensors are preferably distributed substantially uniformly across the cross-section of the conduit passage to provide more accurate gas component measurements. Any suitable gas sensors can be employed.

The controller 220 can be any suitable processor, including a microprocessor, and typically includes a memory for storing measurements, computational control and derivation modules, and other information. Although a digital gas delivery system is depicted in FIG. 2, it is to be understood that the concepts of the present invention work equally well with an analog gas delivery system.

A test gas supply assembly 230 is controlled by the controller 220 and provides a test gas of a desired composition at a desired flow rate. For controlling composition, the assembly 230 includes a plurality of gas storage vessels 234a-n, each having a different gas composition ("G"), and a corresponding plurality of valves ("V") 238a-n controlling flow out of the vessels. For controlling flow rate, the assembly 230 includes a plurality of flow restrictors ("R") 242a-i of different orifice sizes and corresponding flow valves ("V") 246a-i for controlling gas flow through the corresponding flow restrictor 242. Dashed lines represent gas flow lines for transporting gas to the injectors 216 while solid lines represent signaling control lines for conveying digital commands from the controller 220 to the various valves 246a-i and 238a-n.

To illustrate the operation of the test gas supply assembly 230 assume that "X" represents a selected flow rate, that the flow rate through each of the flow restrictors is a product of X with a selected flow factor (e.g., weigh the orifices in a binary scheme, such as the flow rate through valve 242a being 8X, through valve 242b being 4X, through valve 242c being 2X, and through valve 242i being X, which would provide sixteen different flow rates adjustable by a four-bit binary code), and that each of the vessels 234a-n contains a different gas component (e.g., vessel 234a contains carbon monoxide or acetylene, vessel 234b helium or methane, and vessel 234n molecular oxygen). The controller 220 can deliver a gas comprising a mixture of carbon monoxide or acetylene on the one hand and helium or methane on the other at a selected flow rate by opening valves 238a and b and a selected one or combination of valves 246a-i. As will be appreciated, each vessel 234 can include a mixture of gas components or a single vessel containing a selected mixture of gas components can replace all of the vessels depending on the application. The configuration of FIG. 2 can provide a simple, controllable and versatile pulmonary testing device.

The operation of the pulmonary testing device 200 will now be described with reference to FIGS. 2A, and 3-5.

To initiate a test, the controller 220 introduces a test gas mixture through the injectors 216 at a flow rate that provides a test gas volume over a selected period of time that is greater than the volume of gas that the patient will likely inspire over the same time period. The uniform distribution of test gas across the cross-section of the conduit 204 effectively provides a "wall" 250 of test gas that blocks or inhibits the flow of ambient air through the conduit 200 and into the patient's lungs. The requisite gas flow rate through the injectors depends on the number of gas injectors employed.

Figure 5:
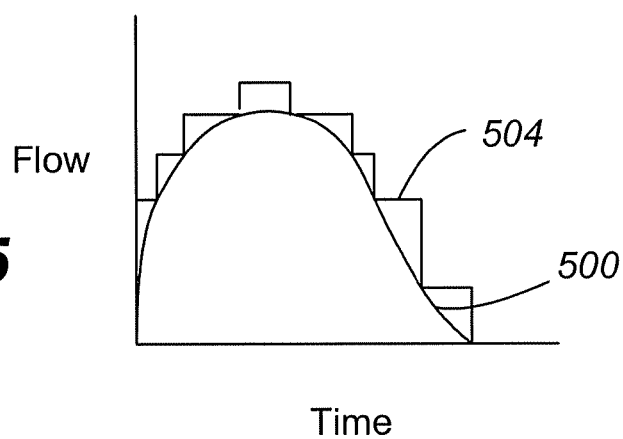
FIG. 5 is a plot of gas flow rate against time for an inspired gas flow.

The patient then commences inspiring the test gas through the mouthpiece 208. As the patient's inspiration rate (or the flow rate through the conduit 204) changes, the controller 220 issues commands to the valves 246a-i as required to simultaneously and equally decrease or increase the flow rates through the injectors to maintain a bulk introduction gas flow rate that is sufficient to compensate for the gas being inspired by the patient. With reference to FIG. 5 for example, the curve 500 represents the collective flow rate through injectors that, at any point in time, is effectively equal to the flow rate through the conduit as measured by the flow rate sensor 156. As can be seen from FIG. 5, the collective flow rate 504 through the injectors is maintained, over a selected time interval, at a magnitude that is greater than the flow rates on the curve over the same interval.

In a preferred embodiment, during any selected time interval the flow rate through the injectors is maintained at a selected flow rate greater than the flow rates on the curve, where the selected flow rate is sufficient to maintain the test gas wall 250. In one embodiment, the controller 220 measures the current flow rate, determines the rate of change of the flow rate over a selected number of preceding time intervals, and, based on this information, predicts a likely flow rate over the subsequent time interval. The control signal sent to the valves 246a-i for valve control in the subsequent time interval is generally based on that prediction.

Figure 3:
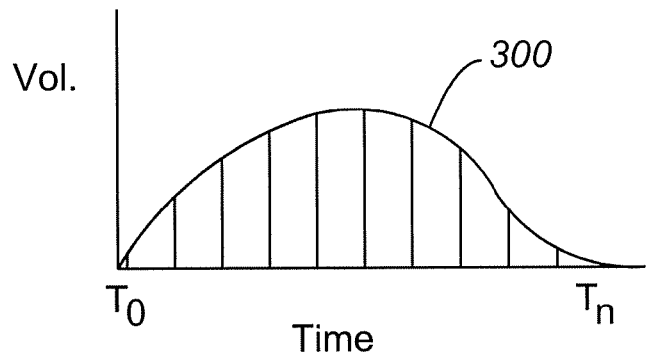
FIG. 3 is a plot of inspired gas volume (vertical axis) against time (horizontal axis) to provide a curve defining a series of gas flow rates.

The inspired and/or expired gas component volumes can be determined using measurements from the flow and gas concentration sensors 156 and 152, respectively. FIG. 3 shows a typical patient inspiration curve 300 for a selected gas component X. The area under the curve represents the total volume of gas component X inspired by the patient over the time interval $T_0$ to $T_n$. The area may be determined using any known mathematical algorithms, such as integration. In a preferred embodiment, the area is determined using the following equation:

$$V_X = \sum \left(\frac{dV_I}{dt} F_X\right)_i \Delta T_i$$

where $V_X$ is the total volume of a selected gas component inspired by the patient, $$\frac{dV_I}{dt}$$

is the inspired flow rate over a sample interval (measured by the gas flow measuring device 156), $F_X$ is the fraction of the inspired gas flow during the sample interval that represents component X (measured by the gas sensors 152), and $\Delta T_i$ is the sample interval (which is usually the time interval between successive measurements). The various products are summed over the duration of the pulmonary test, which varies depending on the type of test being conducted.

Figure 4:
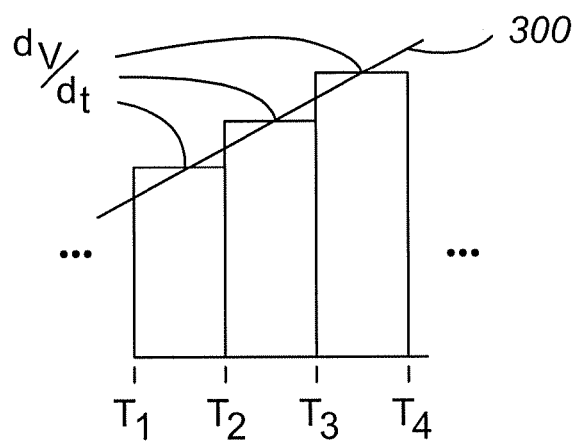
FIG. 4 is an enlarged view of a portion of the curve of FIG. 3.

The equation can be illustrated with reference to FIG. 4. FIG. 4 shows a series of sample time intervals, $T_1$-$T_2$, $T_2$-$T_3$, and $T_3$-$T_4$. The $$\frac{dV_I}{dt}$$

in each sample time interval is the average flow rate measured over each sample interval. As will be appreciated, $$\frac{dV_I}{dt}$$

can be determined in a number of ways, such as the median flow rate and the like. Using this equation, the dead space in the device 200 is substantially unimportant because of the accuracy of the algorithm in determining the volume of each component inspired into the lungs.

The gathered measurements can be used to perform a number of pulmonary tests. For example, the measurements can be used to determine lung volume, such as using gas wash-in methods (e.g., molecular nitrogen washout using molecular oxygen inspiration, methane single breath dilution, and multi-breath equilibration), (capillary and/or membrane) diffusion, such as using carbon monoxide or acetylene absorption coupled with a non-absorbable gas, and other lung mechanics and pulmonary function known to those of ordinary skill in the art. The device 200 is particularly useful in performing one or more of the foregoing tests while the patient is exercising. The device 200 can be lightweight, easily manipulated by the patient, and can provide (without using a new device 200) a varying inspired gas composition depending on the particular test desired.

A number of variations and modifications of the invention can be used. It would be possible to provide for some features of the invention without providing others.

For example in one alternative embodiment, a flow rate of sample gas is injected that is not sufficient to maintain a wall 250 of sample gas. In other words, ambient air is permitted to enter into the conduit 204 for inspiration by the patient while a sample gas is introduced through the injector(s). In this embodiment, the sample gas could be a single gas component or a mixture of gas components. The gas analyzers would permit the fraction of the inspired volume represented by a target gas component to be readily and accurately determined notwithstanding the presence of non-test gas components from the ambient atmosphere. This embodiment has the advantage of using a lesser volume of sample gas in the test, which can represent a significant cost savings. Patient safety can be ensured where a single component sample gas is used, such as a single component carbon monoxide or acetylene gas, by using a vessel 234 of a sufficient small volume that if the device 200 malfunctioned and introduced the entire volume of the vessel 234 into the conduit 204 the patient's health would not be compromised. Alternately, the concentration of the gas component can be limited to a safe maximum value such that it will not pose a health hazard even under prolonged breathing conditions.

Figure 6:
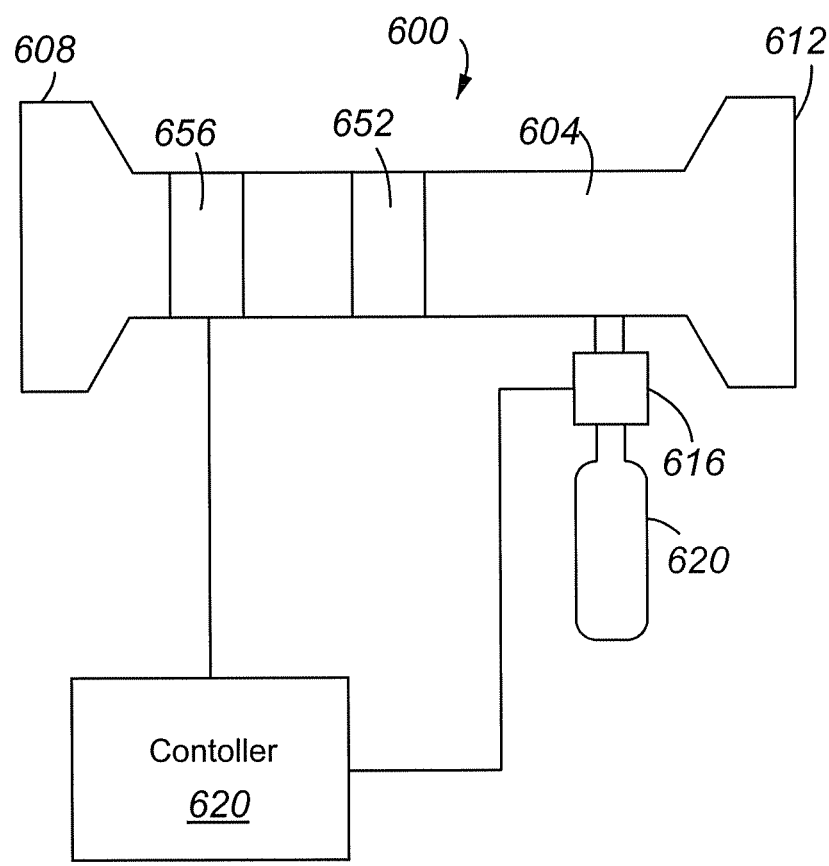
FIG. 6 is a cross-sectional view of a pulmonary testing device according to a second embodiment of the present invention.

An alternative embodiment in accordance with embodiments of the present invention is illustrated in FIG. 6. In the depicted embodiment, a small quantity of the test gas component(s) is stored in a small gas cartridge 620 at high concentrations (up to 100%). For example, a 2 ml gas cartridge storing 100% CO at 50 psi can provide over 1000 ppm of CO to a patient with an inspiratory capacity of 5 liters. The gas cartridge 620 is connected to the breathing conduit 604 through a valve mechanism. The valve mechanism can be an electrically actuated solenoid valve 616 or other suitable mechanisms. The valve 616 is actuated after the initiation of inspiring effort at an appropriate point during the test. The test gas stored in the gas cartridge 620 is discharged into the breathing conduit 604 to be inhaled by the patient. A restrictor in series with the valve 616 can also be employed to extend the gas discharge time to a few seconds to limit the peak concentration of gas component thereby reducing the dynamic range requirements for the gas sensors/analyzers 652. Similar to other embodiments, the flow sensor 656 and the gas sensors/analyzers 652 measure the total volume of test gas component inhaled. This embodiment has the advantage of eliminating the need for gas lines connecting the test gas source and the pulmonary test device. The small gas cartridge 620, preferably a single use item, can be easily stored and procured. The small size of the cartridge also ensures patient safety even if the entire content is discharged rapidly.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A pulmonary testing device, comprising:
 a body with first and second ends, the first end comprising a mouthpiece for a patient and the second end being open to the ambient atmosphere;
 at least two test gas injectors positioned proximate to the second end forming a junction between each of the at least two test gas injectors and the body of the device, the injectors each being angled away from the first end at an angle measured relative to a centerline of the body and wherein the angle is less than 90 degrees, whereby a test gas is introduced into the body via the junctions at a direction away from the first end;
 a flow rate measuring device operable to determine a flow rate of gas being at least one of inspired and expired by the patient;
 a gas analyzer operable to measure a concentration of a selected test gas component during inhalation; and
 a controller operable to determine a volume of the selected test gas component, wherein the controller determines a volume of the selected test gas component by measuring the gas flow rate and using the concentration of the selected test gas-component measured by the gas analyzer.

2. The testing device of claim 1, further comprising:
 a plurality of first valves in communication with a plurality of flow restrictors, the flow restrictors each imparting a different degree of flow resistance; and
 a plurality of second valves in communication with a plurality of corresponding vessels, each of the vessels comprising a gas having a composition different than the gases in the other vessels, wherein the first and second valves are controlled by the controller to provide a test gas of a desired gas composition and/or flow rate.

3. The testing device of claim 1, wherein the first and second ends lie along a centerline of the device.

4. The testing device of claim 1, wherein the controller is configured to change a composition of the test gas while the mouthpiece is in the patient's mouth.

5. The testing device of claim 1, wherein the controller is configured to change a flow rate of the test gas.

6. The testing device of claim 1, wherein the controller comprises a logical circuit operable to determine an inspired volume of a selected gas component of the test gas using the following equation:

$$V_X = \sum \left(\frac{dV_I}{dt} F_X\right)_i \Delta T_i$$

where $V_X$ is the total volume of the selected gas component X inspired by the patient, $$\frac{dV_I}{dt}$$

is the inspired flow rate over a sample interval (measured by the flow rate measuring device), $F_X$ is the fraction of the inspired gas flow during the sample interval that represents the selected component X (measured by the gas analyzer), $\Delta T_i$ is a sample interval, i is the reference indicating which member the sample interval represents in a set of sample intervals.

7. The testing device of claim 1, wherein the angle at which the at least two injectors is angled away from the first end is between about 10 degrees and about 75 degrees.

8. A pulmonary testing device, comprising:
- a body with a first end and multiple second ends, the first end comprising a mouthpiece for a patient and at least one of the multiple second ends being open to the ambient atmosphere;
- at least two test gas injectors positioned proximate to at least one of the second ends forming a junction between each of the at least two test gas injectors and the body of the device, the injectors each being angled away from the first end at an angle measured relative to a centerline of the body and wherein the angle is less than 90 degrees, whereby a test gas is introduced into the body via the junctions at a direction away from the first end;
- a flow rate measuring device operable to determine a flow rate of gas being at least one of inspired and expired by the patient;
- a gas analyzer operable to measure a concentration of a selected test gas component during inhalation; and
- a controller operable to determine a volume of the selected test gas component, wherein the controller determines a volume of the selected test gas component by measuring the gas flow rate and using the concentration of the selected test gas-component measured by the gas analyzer.

9. The testing device of claim 8, further comprising:
- a plurality of first valves in communication with a plurality of flow restrictors, the flow restrictors each imparting a different degree of flow resistance; and
- a plurality of second valves in communication with a plurality of corresponding vessels, each of the vessels comprising a gas having a composition that differs from gases in each of the other plurality of vessels, wherein the first and second valves are controlled by the controller to provide a test gas of at least one of a desired gas composition and flow rate.

10. The testing device of claim 8, wherein the angle at which the at least two injectors is angled away from the first end is between about 10 degrees and about 75 degrees.

* * * * *